United States Patent [19]
Sanders et al.

[11] Patent Number: 5,609,615
[45] Date of Patent: Mar. 11, 1997

[54] IMPLANTABLE CARDIAC STIMULATION DEVICE WITH WARNING SYSTEM AND CONDUCTIVE SUTURE POINT

[75] Inventors: Richard S. Sanders, Houston; Patrick J. Paul; David Prutchi, both of Lake Jackson, all of Tex.

[73] Assignee: Intermedics, Inc., Angleton, Tex.

[21] Appl. No.: 532,929

[22] Filed: Sep. 22, 1995

[51] Int. Cl.⁶ ..................................................... A61N 1/37
[52] U.S. Cl. ................................ 607/36; 607/27; 607/29; 607/63; 607/116; 607/132
[58] Field of Search .......................... 607/4, 5, 9, 27–29, 607/36, 63, 116, 132, 48, 119, 118

[56] References Cited

U.S. PATENT DOCUMENTS

| | | |
|---|---|---|
| 4,140,131 | 2/1979 | Dutcher et al. . |
| 4,295,474 | 10/1981 | Fischell ........................ 607/5 |
| 4,345,603 | 8/1982 | Schulman .................... 607/29 |
| 4,404,972 | 9/1983 | Gordon et al. . |
| 4,407,288 | 10/1983 | Langer et al. ............... 607/4 |
| 4,539,992 | 9/1985 | Calfee et al. . |
| 5,076,272 | 12/1991 | Ferek-Petric . |
| 5,332,400 | 7/1994 | Alferness .................... 607/5 |

FOREIGN PATENT DOCUMENTS

| | | | |
|---|---|---|---|
| 534782 | 3/1993 | European Pat. Off. .............. | 607/36 |

*Primary Examiner*—Jeffrey R. Jastrzab
*Attorney, Agent, or Firm*—John R. Merkling

[57] ABSTRACT

A cardiac simulator including a patient warning apparatus, having an electrically conductive suture point in electrical communication with the patient warning apparatus. An electrically conductive suture passed through the suture point connects said stimulator mechanically and electrically to excitable tissue such as skeletal tissue. Inside the suture point is a connection for assuring a reliable electrical contact between the suture point and the suture. The cardiac stimulator automatically alters the peak voltage of its output stimulus whenever a condition exists requiring patient notification or warning. A specialized shunt circuit mounted within the stimulator or in the header of the stimulator re-directs electrical current from the standard stimulation electrode to the electrically conductive suture point. A controlled switch may be mounted within a hermetically sealed can of the stimulator to re-direct a stimulation pulse to the suture point. The controlled switch could also be mounted in the header. A dedicated stimulation circuit could also be used. The connection inside the suture point may comprise conductive metal fingers or bristles, a toroidal, multi-filar or woven conductor or an electrically conductive polymer.

24 Claims, 7 Drawing Sheets

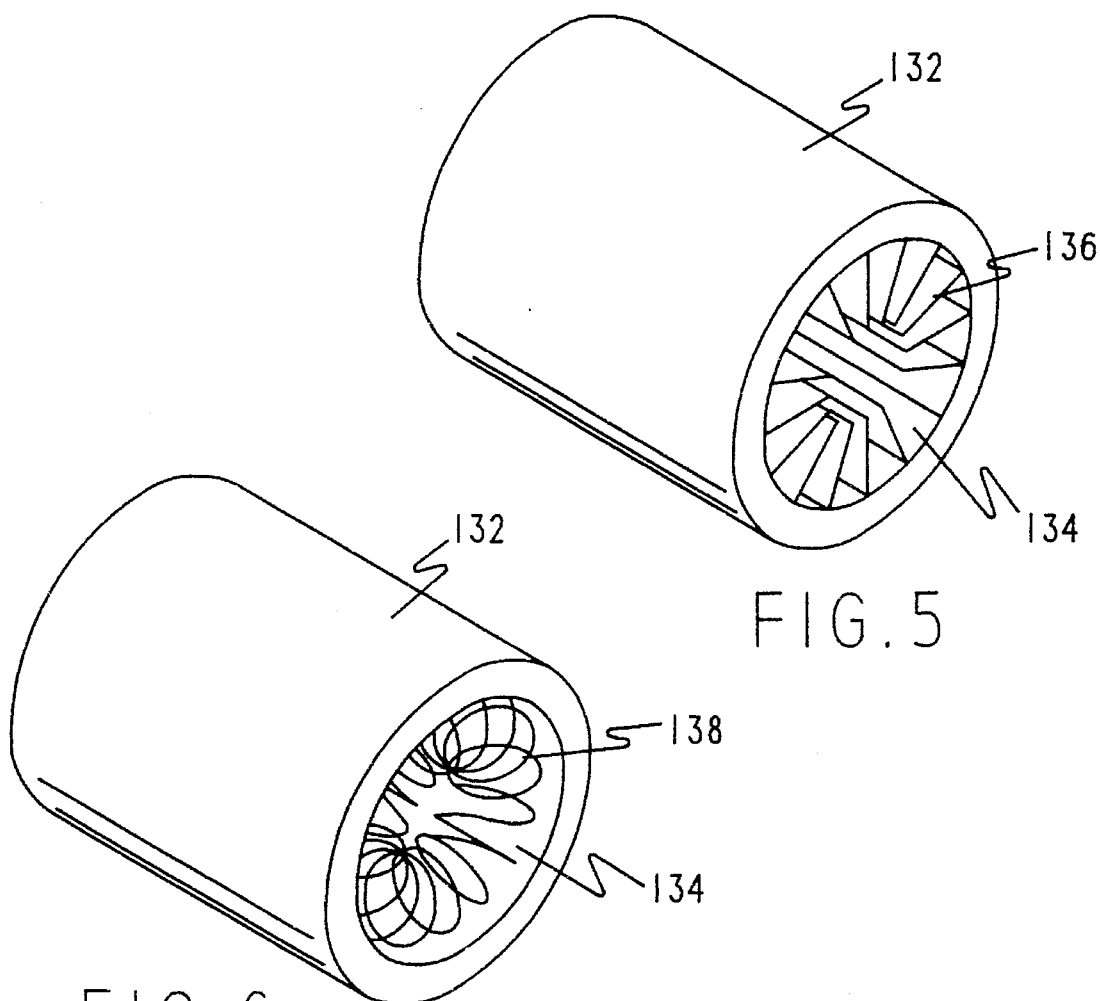
FIG. 5
FIG. 6
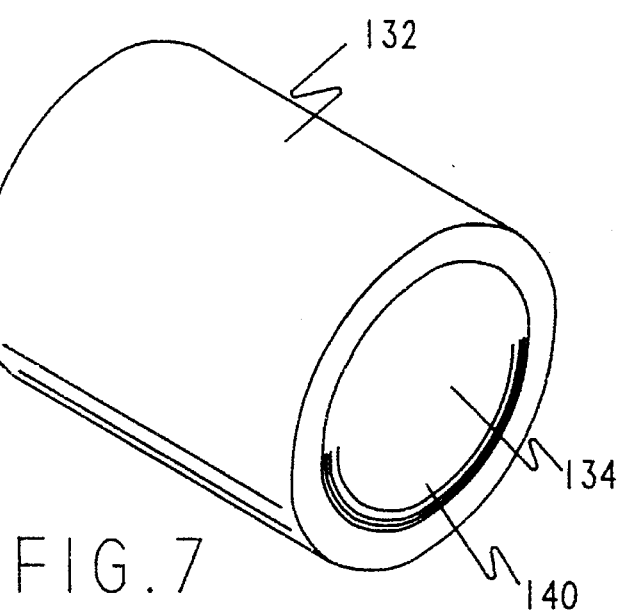
FIG. 7

IMPLANTABLE CARDIAC STIMULATION DEVICE WITH WARNING SYSTEM AND CONDUCTIVE SUTURE POINT

FIELD OF OUR INVENTION

Our invention relates to cardiac pacemakers and other cardiac stimulators which monitor the operation of the heart and stimulate the heart tissue as required to maintain the proper operation of the heart, including implantable cardioverters and defibrillators. In particular, our invention relates to an implantable cardiac stimulating system with the capability of alerting or warning a patient of certain conditions or situations, including, without limitation, battery depletion, lead malfunction, or the eminent delivery of therapy.

BACKGROUND OF OUR INVENTION

It has long been known that the heart muscle provides its pumping function in response to electrical events which occur within the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle. Synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood. The required synchronized activity of such diseased hearts can be maintained by any implanted cardiac pacemaker which applies synchronized stimulating pulses to either the atrium or ventricle or both.

A diseased heart may also beat unusually quickly, a condition known as tachycardia, or may lapse into a rapid, disorganized quivering known as fibrillation. The former condition is undesirable; the latter condition may be fatal. To correct these conditions, implantable cardioverters and defibrillators have been proposed. Like the related cardiac pacemaker, these devices monitor the electrical condition of the heart and provide a corrective electrical therapy to correct the improper heart function. The three functions of pacing, cardioverting and defibrillating, or any of them, may be incorporated into a single device, generically, an implantable cardiac stimulator.

Cardiac stimulators are battery powered and, consequently, have a finite life before battery depletion may be expected. In addition to the battery, other components of the cardiac stimulation system may fail, such as leads, electrodes, or other system components. As an example of another type of change, the sensitivity of a patient's heart to electrical stimulation may change over time, altering the so-called threshold level for electrical stimulation. Such change of condition requires adaptation of the therapy delivered by the implantable cardiac stimulator, either automatically or by intervention by the attending physician. In any of these situations, or others, it may be deemed desirable to alert the patient to a changed condition so that action may be taken. For example, a pacemaker may detect the approaching end of life of its battery, in a known manner. It is desirable to alert the patient to this condition. Moreover, in the case of implantable defibrillators, delivery of therapy can be traumatic. It is sometimes deemed important to alert the patient to the prospect of eminent delivery of therapy.

Cardiac stimulators which alert or warn the patient of such conditions are known in the art. For example, such a device is described by Dutcher, et al. in U.S. Pat. No. 4,140,131. In the device described by Dutcher, et al., a device-controlled switch is activated to enable a specialized electrode adjacent the pacemaker to stimulate the patient's muscles to twitch. The nature of the electrode is not described in detail, but Ferek-Petrick, in U.S. Pat. No. 5,076,272, described the electrode of Dutcher, et al., as an auxiliary electrode surrounded by the indifferent electrode and fixed on the pacemaker can. In contrast, Ferek-Petrick, in U.S. Pat. No. 5,076,272, describes a cardiac stimulator with patient warning with an electrode affixed to the header of the stimulator. Another electrode is described in U.S. patent application Ser. No. 08/426,949, filed Apr. 21, 1995, by some of us (Paul and Prutchi), also assigned to Intermedics, Inc.

We have found that a suture point or hole, commonly provided on a header of a stimulator, can be modified to provide an electrical connection. An electrically conductive suture can then be used to secure the stimulator and to provide a connection for stimulus of the skeletal muscles of the patient to produce an effective twitch.

It is an object of our invention, therefore, to provide a cardiac stimulator with a patient warning apparatus. It is also an object of our invention to produce an implantable cardiac stimulator with an electrically conductive suture point, electrically connected to said patient warning means. Another object of our invention is to provide an electrically conductive suture for use with the conductive suture point. It is a further object of our invention to provide an auxiliary electrode for the purpose of providing patient warning signals by stimulating excitable tissue of the patient, for example, nerve ends or skeletal muscles. Another object of our invention is to provide for an effective implantable cardiac stimulation system with a reliable patient warning apparatus.

SUMMARY OF OUR INVENTION

In view of the foregoing, we have invented a cardiac simulator including a patient warning apparatus, having an electrically conductive suture point in electrical communication with said patient warning apparatus. An electrically conductive suture passed through the suture point connects said stimulator mechanically and electrically to excitable tissue such as skeletal muscle. Inside the suture point is connection means for assuring a reliable electrical contact between said suture point and said suture. In our preferred embodiment, the cardiac stimulator is an implantable pacemaker or defibrillator or combination which can be programmed. In one embodiment, the cardiac stimulator is an implantable pacemaker or defibrillator or combination which can be programmed to automatically alter the peak voltage of its output stimulus, in particular, to increase the peak voltage of the output stimulus whenever a condition exists requiring patient notification or warning. A specialized shunt circuit mounted within the stimulator or in the header of the stimulator re-directs electrical current from the standard stimulation electrode implanted in or near the patient's heart to the electrically conductive suture point in the presence of a stimulation pulse with a voltage at or above a preselected level. Suitable circuits are more particularly described in U.S. patent application Ser. No. 08/426,949.

Alternatively and preferably, a controlled switch may be mounted either within a hermetically sealed can, as we prefer, or in the header of the stimulator to re-direct a stimulation pulse to the suture point. A dedicated stimulation circuit could also be used, but for cost reasons we do not prefer this alternative.

The connection means inside the suture point may comprise, for example, conductive metal fingers or bristles, a toroidal, multi-filar or woven conductor or an electrically conductive polymer. A reliable electrical connection should be made to the suture, so that a good electrical path exists between the stimulator and excitable tissue.

With the foregoing in mind, we will now describe the preferred embodiment of our invention with respect to the accompanying drawings.

BRIEF DESCRIPTION OF THE DRAWINGS

FIG. 5 is a perspective view of a first embodiment of the suture hole of the cardiac stimulator of FIG. 1.

FIG. 6 is a perspective view of a second embodiment of the suture hole of the cardiac stimulator of FIG. 1.

FIG. 7 is a perspective view of a third embodiment of the suture hole of the cardiac stimulator of FIG. 1.

DETAILED DESCRIPTION OF OUR PREFERRED EMBODIMENT

Figure 1:
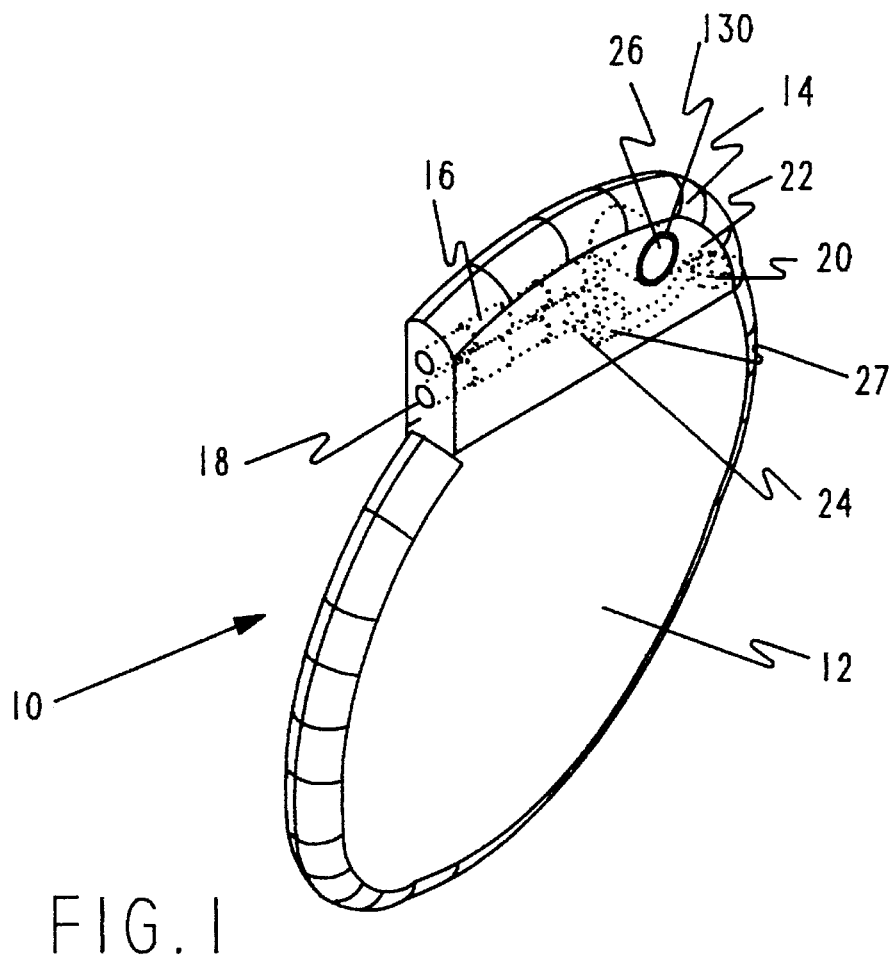
FIG. 1 is a perspective drawing of a cardiac stimulator with electrically conductive suture point according to our invention.

FIG. 1 is a perspective drawing of a cardiac stimulator, generally designated 10, according to our invention. We have illustrated our invention in connection with a dual chamber pacemaker, but our invention is equally applicable with other implantable cardiac stimulators such as cardioverters and defibrillators, as are known in the art. The cardiac stimulator 10 comprises a hermetically sealed case or can 12 which, in a known fashion, contains batteries and electrical circuitry. A header 14, attached to the can 12, has two sockets 16, 18 to which leads can be mechanically and electrically connected. Leads are commonly used to place the cardiac stimulator 10 in electrical communication with the heart or other body tissues. Electrical conductors 22, 24 provide an electrical connection between the sockets 16, 18 and the circuitry inside the can 12 through a feed through 20. In the illustrated dual chamber pacemaker, one channel of stimulation circuitry connected to socket 18 would usually be used to sense and stimulate the ventricle of the heart, while another channel of stimulation circuitry connected to socket 16 would usually be used to sense and stimulate the atrium of the heart. In our invention one channel, for example the atrial channel, is also used for warning the patient of certain conditions, such as low battery power, through an electrically conductive suture point or hole 26. The conductor 22 for the atrial channel could be connected through a shunt circuit 27 or through a controlled switch as more fully explained below. Alternatively, a dedicated stimulation channel could be connected to the conductive suture point. The shunt circuit 27 or controlled switch may be located in the header, as shown in FIG. 1, or may be housed within the can 12, as suggested diagrammatically in FIG. 2, and FIG. 3. We prefer that the shunt circuit 27 or controlled switch be housed within the can.

Figure 2:
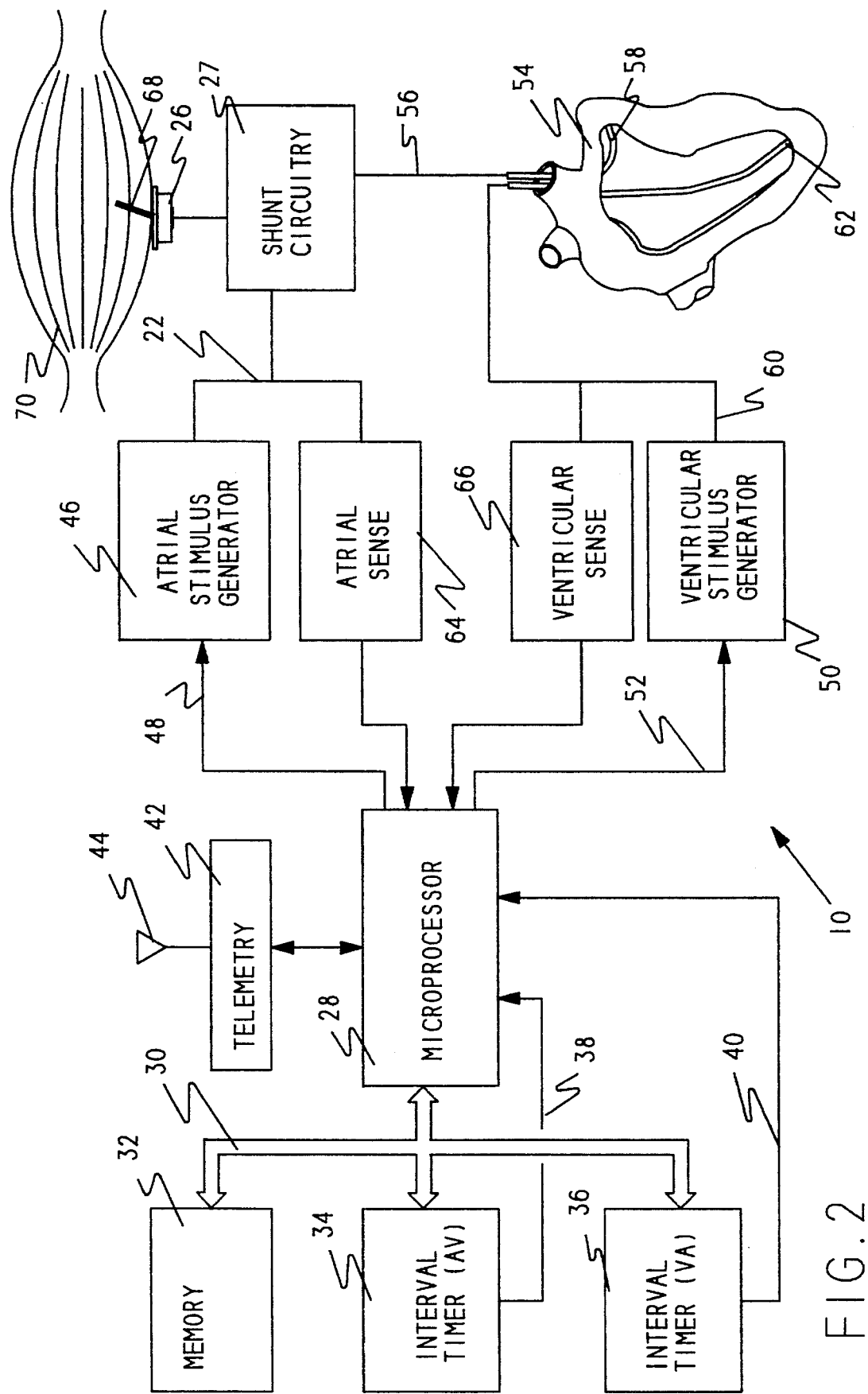
FIG. 2 is a block diagram of a first embodiment of a cardiac stimulation system according to our invention.

As shown in FIG. 2, in the can 12 of the cardiac stimulator 10, a microprocessor 28 preferably provides control and computational facilities. It will be appreciated that other forms of circuitry, such as analog or discrete digital circuitry, can be used in place of the microprocessor 28. However, a microprocessor is preferred for its miniature sized and flexibility, both of which are of critical importance for the implantable systems in which it is envisioned our invention will find use. More particularly, a cardiac stimulator having a microprocessor can usually be re-programmed to utilize our invention without additional structural changes, with the exception of the provision of the shunt circuit 27 or the controlled switch and the conductive suture point 26, to be described hereafter. A particularly energy efficient microprocessor which is designed specifically for use in pacemakers is fully described in Gordon, et al, U.S. Pat. No. 4,404,972, which is assigned to the assignee of our invention. The disclosure thereof is incorporated herein by reference.

The microprocessor 28 has input/output ports connected in a conventional manner via a bi-directional bus 30 to memory 32, an AV interval timer 34, and a VA pacing interval timer 36. In addition, the AV interval timer 34 and VA interval timer 36 each has an output connected individually to a corresponding input port of the microprocessor 28 by lines 38 and 40 respectively. Memory 32 preferably includes both ROM and RAM. The microprocessor 28 may also contain additional ROM and RAM as described in Gordon, et al., above. Generally, the pacemaker operating routine is stored in ROM or EPROM memory. RAM stores various programmable parameters and variables used in conjunction with the pacemaker operation. The AV and VA interval timers 34, 36 may be external to the microprocessor 28, as illustrated, or internal thereto, as described in Gordon, et al., above. The timers 34, 38 are conventional up or down counters of a type initially loaded with count value and count up to or down from the value and output a roll-over bit on completing the programmed count.

The microprocessor 28 preferably has an input/output port connected to a telemetry interface 42. The implanted cardiac stimulator 10 is thus able to receive pacing, rate control, or other parameters from an external programmer through an antenna 44 and to send data to an external receiver if desired. Many suitable telemetry systems are known to those skilled in the art. One such system and coding arrangement is described in Calfee, et al. U.S. Pat. No. 4,539,992 which is also assigned to the assignee of our invention. That description is incorporated therein by reference.

Microprocessor output ports are connected to the input of an atrial stimulus pulse generator 46 by a control line 48. Similarly, a ventricular stimulus generator 50 is connected to the microprocessor by a control line 52. The microprocessor 28 transmits pulse parameter data, such as pulse amplitude and width, as well as enable/disable and pulse initiation codes to the atrial and ventricular stimulus generators 46, 50 along their control lines 48, 52 respectively. The atrial stimulus generator 46 is connected to the heart 54 by a first lead 56 with an electrode 58. Similarly, the ventricular stimulus generator 50 is connected to the heart 54 by a second lead 60 with a corresponding electrode 62. The electrical condition of the heart must also be sensed and that condition must be transmitted to the microprocessor 28. For this purpose, an atrial sense amplifier 64 is connected between the lead 56 and the microprocessor 28. Similarly, a ventricular sense amplifier 66 is connected between the lead 60 and the microprocessor 28. The atrial and ventricular sense amplifiers 64, 66 detect occurrences of P waves and R waves respectively. The cardiac stimulator 10 of our invention is also provided with at least one electrically conductive suture hole or point 26. In the illustrated embodiment the suture point 26 is connected through the shunt circuit 27 to the atrial or first conductor 22, but it could equally well be connected to the ventricular conductor 24 through an appropriate shunt circuit. Also, two or more suture points could be provided. The suture point 26 is connected to the shunt circuitry 27 which allows a relatively high voltage stimulating pulse to be passed through an electrically conductive suture 68 attached to excitable tissue 70 of the patient, rather than or in addition to the electrode 58. The excitable tissue could be skeletal muscle, a nerve ending, or other tissue capable of a perceptible physiologic reaction in response to stimulation.

Figure 8:
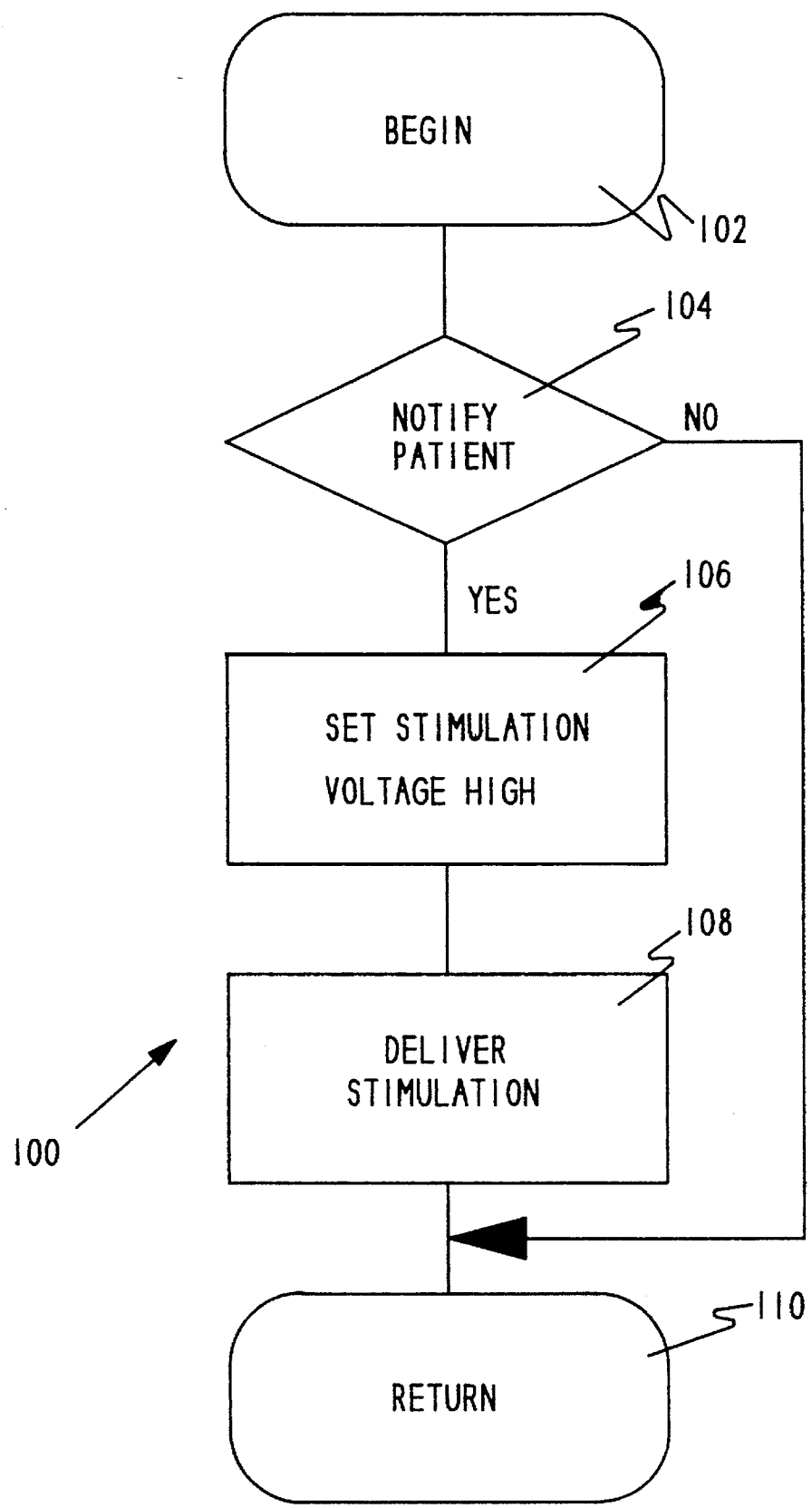
FIG. 8 is a flow chart for a first program to be implemented in the cardiac stimulation system of FIG. 2.

To utilize a shunt circuit 27, a pacemaker is programmed to produce a high-voltage stimulation whenever it is desired to notify the patient of a condition. In prior art devices such as that disclosed in U.S. Pat. No. 5,076,272, various conditions requiring patient notification or warning have heretofore been identified. In the pacemaker, a notification program, such as that indicated at 100 in FIG. 8, is needed. In addition to other standard pacemaker or cardioverter programming, a program segment illustrated at 100 would begin 102 and pass to a test 104 to inquire whether the patient should be notified or not. This program sequence could be a single test controlling a flag, or it might involve multiple tests for different conditions recognized by pacemaker programming and identified in an appropriate manner, such as by setting a flag. These tests could include battery voltage level, presence of inappropriate tachycardia, or eminence of an impending defibrillation shock or other therapy, among other indicators. If there is no condition existing justifying notification or warning of the patient, no further action need be taken in this segment of the microprocessor programming and the program control can branch around the next steps. If it is desired, however, to notify the patient, the microprocessor would adjust 106 the output voltage of the relevant stimulus generator to output impulse at a voltage above a predetermined level. With the voltage set high, the pacemaker would then deliver either an ordinary or a specialized sequence of paces 108 through the ordinary output channel of the pacemaker. However, because of the existence of the shunt circuit 27 between the conductor 22 and the conductive suture point 26, a large portion of the high voltage stimulation would be redirected away from the heart to the excitable tissue, for example, to a voluntary muscle. After delivery of the relevant stimulation for a preselected period, program control would return 110 to additional standard stimulator programming.

Figure 10:
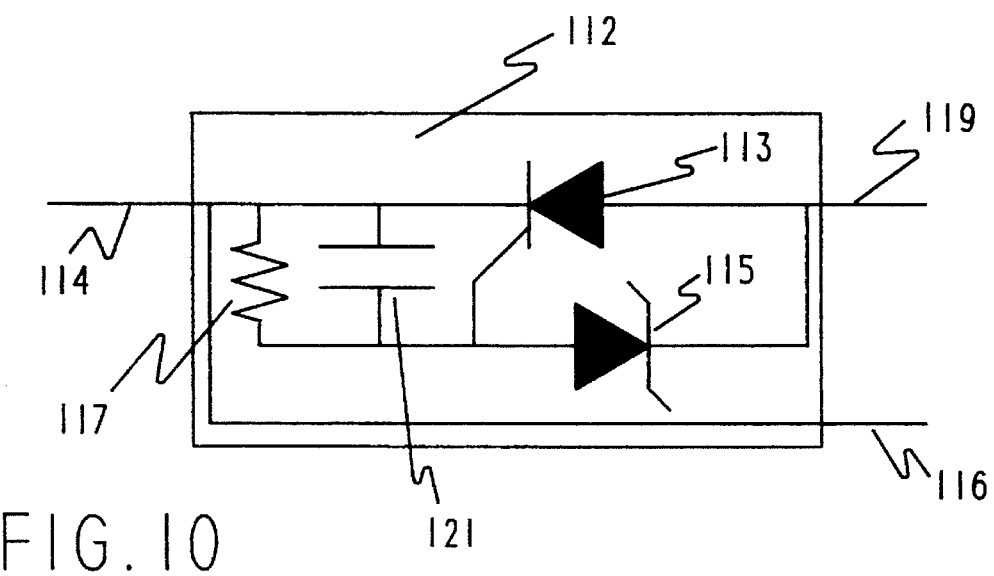
FIG. 10 is a schematic diagram of a shunt circuit for use with the first cardiac stimulation system of FIG. 2.

An embodiment 112 of a shunt circuit 27 sensitive to output voltage levels is illustrated in FIG. 10. Further embodiments are disclosed in U.S. patent application Ser. No. 08/426,949 and are incorporated herein by reference. In FIG. 10, the embodiment 112 of the shunt circuit comprises an input line 114 connected directly to an output 116 for the conductor 22 and to a semiconductor controlled rectifier or SCR 113, or other suitable solid state device or switching means. The SCR 113 is tripped by a zener diode 115 whenever the pacing pulse amplitude exceeds the threshold voltage of the diode 115. Current flow through the diode 115 operates to open the SCR 113 to current flow. Because of a biasing resistor 117, the SCR 113 then remains open for a brief period of time dependent on the component values, providing a low impedance path to the output 119 to the suture point 26. This implementation has the advantage that the pulse amplitude delivered to the voluntary muscle is higher than that possible through the use of a single zener diode or back-to-back zener diodes. The resistor 117 reduces the sensitivity of the SCR to the current passing through the zener diode, even when operating at its threshold voltage. Careful selection of the operating parameters of the SCR 113 and zener diode 115 would reduce the need for the resistor 117. In addition, a small-value capacitor 121 may be needed to filter voltage transients that could cause the shunt circuitry to trigger erroneously. So long as the output voltage of the pacemaker remains below the break-down voltage of the zener diode 115, all current would be directed to the cardiac electrode and would be used to stimulate the heart. Whenever patient notification is needed, on the other hand, the output voltage would be increased by the microprocessor to a level in excess of the break-down voltage. At that point, the zener diode 115 would become conductive, opening the SCR 113, and a portion of the stimulating pulse would be passed to the auxiliary electrode, causing the voluntary muscle to which it was attached to twitch.

Figure 3:
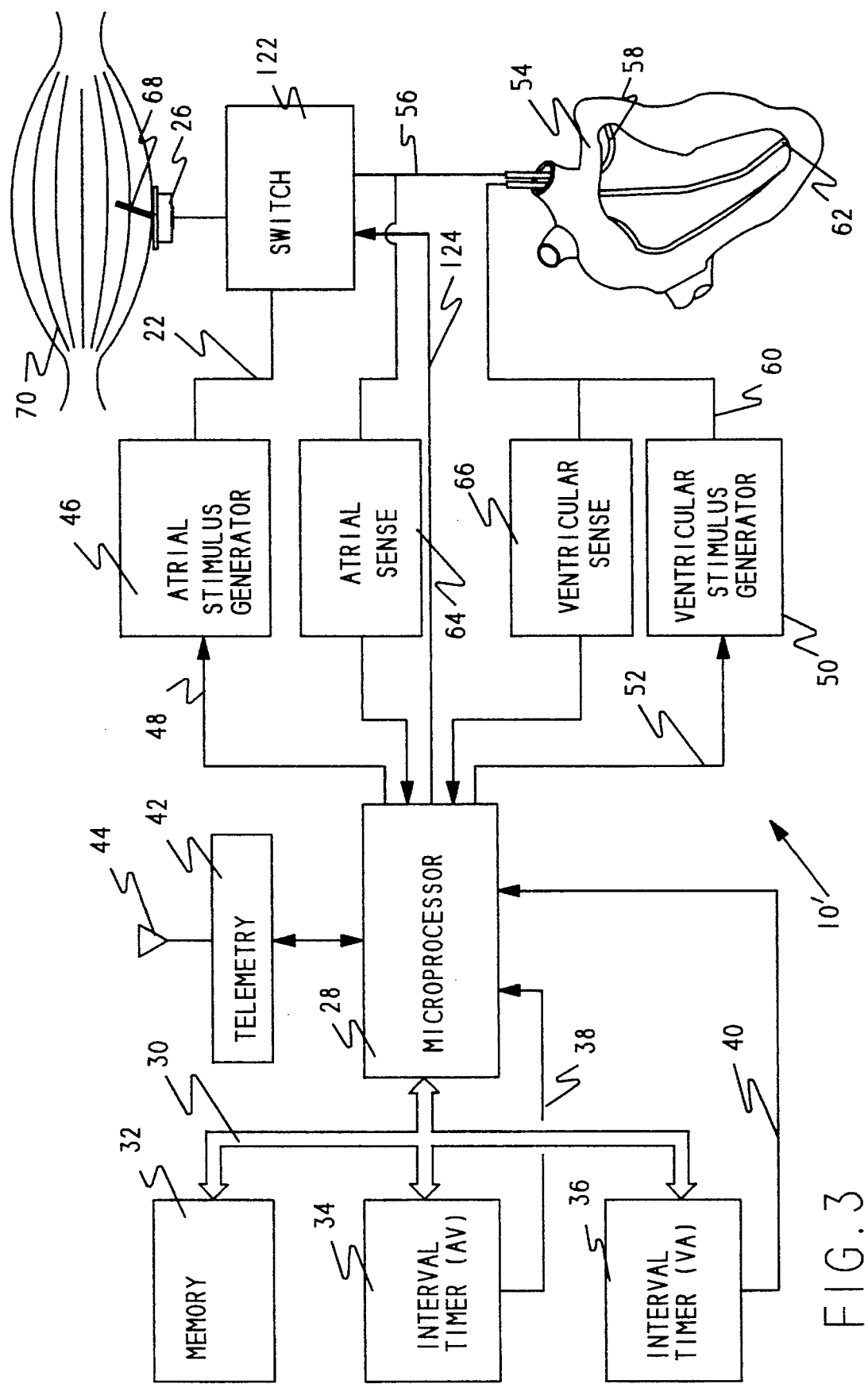
FIG. 3 is a block diagram of a second embodiment of a cardiac stimulation system according to our invention.

An alternative embodiment of the stimulator is illustrated diagrammatically in FIG. 3 as 10'. The stimulator 10' of FIG. 3 is substantially similar to the stimulator 10 of FIG. 2, with the exception of the use of a controlled switch 122 instead of the shunt circuit 27. Similar components have been labeled with the same numerals used in connection with FIG. 2 and have the same functions and characteristics. They will not, therefore, be described again here. The controlled switch 122 comprises a solid state double pole, single throw switch controlled by the microprocessor 28 through a control line 124. When the patient is to be warned, the microprocessor disconnects the lead 56 and electrode 58 and connects the conductive suture point 26. The output of the atrial stimulus generator is then directed into the excitable tissue 70, rather than into the heart 54. The controlled switch 122 is preferably mounted within the can 12 of the stimulator 10, although it could also be mounted in the header 14 if desired.

Figure 9:
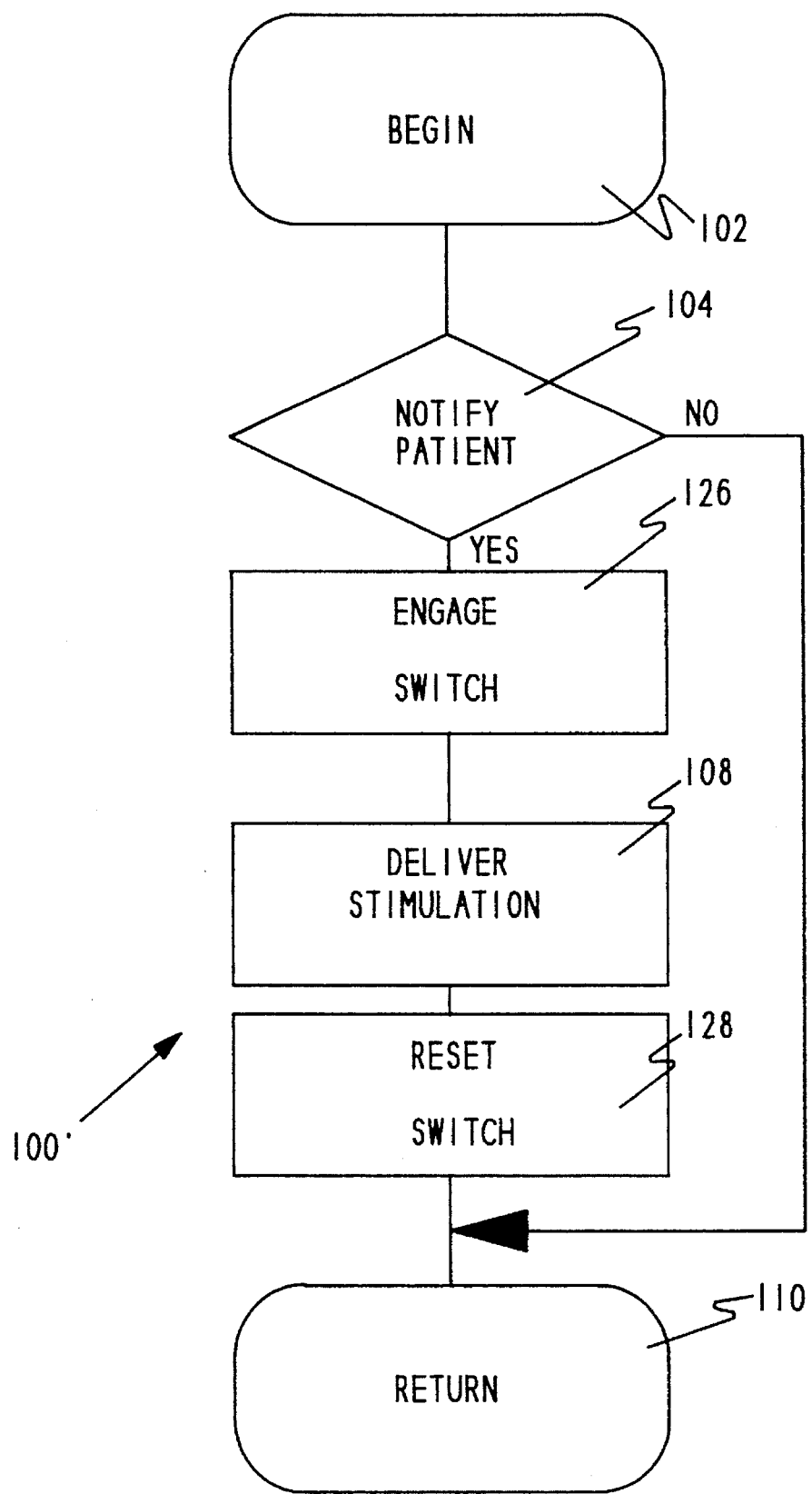
FIG. 9 is a flow chart for a first program to be implemented in the cardiac stimulation system of FIG. 3.

As in the stimulator 10, a notification program, such as that indicated at 100' in FIG. 9, is needed for the stimulator 10'. As before, similar steps found in FIG. 8 are indicated with identical numerals in FIG. 9. Instead of increasing the stimulation voltage if the patient is to be notified, however, the microprocessor 28 engages 126 the switch 122. After the stimulation has been delivered 108, the microprocessor resets 128 the switch before returning 110 to other programming.

Figure 4:
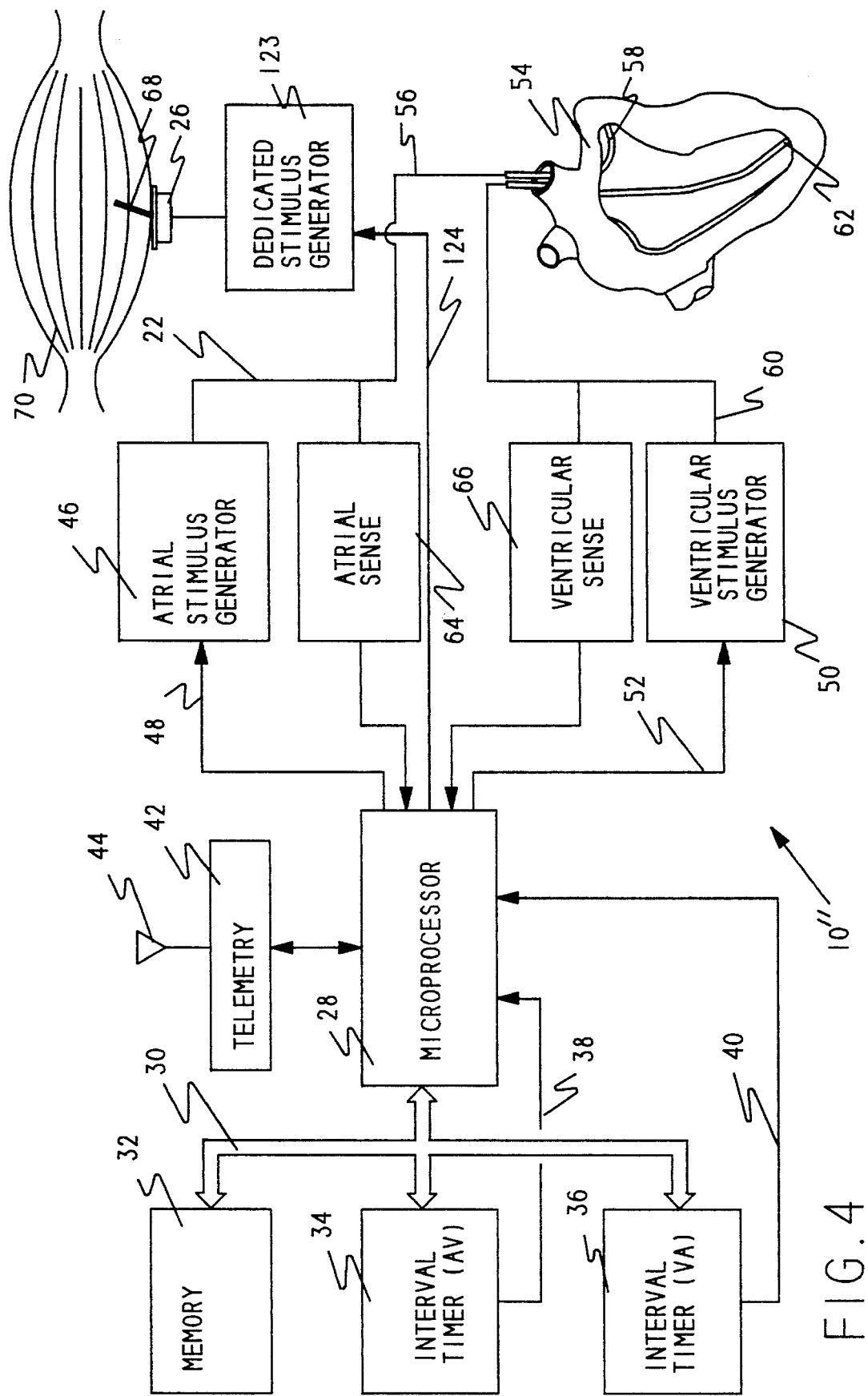
FIG. 4 is a block diagram of a third embodiment of a cardiac stimulation system according to our invention.

The shunt circuit 27 or the controlled switch 122 re-direct a stimulus to excitable muscle. Alternatively, a dedicated stimulus generator 123, as shown in FIG. 4 as a third embodiment 10" of the stimulator, could be used only for generating a warning signal. In such a case, the output of the stimulus generator 123 would be connected directly to the conductive suture point 26 and the stimulus generator 123 would produce an output only when the patient was to be notified or warned of a changed condition.

The conductive suture point 26 of our invention comprises a through bore 130 through the stimulator 10, preferably through the header 14. An electrically conductive lining 132 lies within the through bore 130. The lining 132 may extend completely or partially through the bore 130. Within the lining 132, we have provided electrical contact means 134. The electrical contact means can have several forms. For instance, as shown in FIG. 5, circumferential bristles 136 or springs may be provided extending from the lining 132 towards the center of the bore 130. When the electrically conductive suture 68 is threaded though the bore 130 of the suture point 26 and through excitable tissue, it will electrically engage the lining 132 and the bristles 134 to make a reliable electrical contact between the stimulator 10 and the excitable tissue 60. A suitable multifilament stainless steel suture is available from Davis-Geck Co. In FIG. 6 a braided conductor 138 is illustrated as electrical contact means 134. Braided or multifilament coiled wire is formed into a toroidal configuration and secured within the lining 132 by, for example, welding. Another electrical contact means 134 is an electrically conductive polymer plug 140, shown in FIG. 7. A needle on the suture 62 permits the suture to penetrate the plug 140 and be drawn through the suture point 26, forming the desired reliable electrical connection between the stimulator 10 and the excitable tissue 70.

Our invention may be embodied in other specific forms without departing from the spirit or essential characteristics thereof. Present embodiment is therefore considered in all respects to be illustrative and not restrictive, the scope of our invention being indicated by the appended claims whether by the foregoing description and all changes which come within the meaning and range of equivalency of the claims are therefore intended to be embraced therein.

We claim as our invention:

1. An implantable cardiac stimulator comprising means for producing a cardiac therapy, a stimulator case containing said therapy producing means, at least one electrode adapted to be implanted adjacent a patient's heart for delivering said therapy to the heart, a cardiac stimulation lead electrically connecting said therapy producing means to said electrode, means for detecting a predetermined condition, means for producing a physiologic stimulation to warn said patient of said detected condition, suture point means for providing an electrically conductive suture point on said stimulator case, said suture point means being adapted to receive a suture for securing said stimulator case to adjacent tissue of a patient, and an electrical conductor providing electrical communication between said means for producing a physiologic stimulation and said suture point means.

2. The implantable cardiac stimulator according to claim 1 wherein said suture point means comprises a though bore in said stimulator case.

3. The implantable cardiac stimulator according to claim 2 wherein said suture point means further comprises electrical contact means for securing a reliable electrical contact between said suture point means and an electrically conductive suture.

4. The implantable cardiac stimulator according to claim 3 wherein said electrical contact means comprises at least one spring contact within said bore.

5. The implantable cardiac stimulator according to claim 4 wherein said at least one spring contact comprises a plurality of bristles extending radially inwardly into said bore.

6. The implantable cardiac stimulator according to claim 3 wherein said electrical contact means comprises a coiled wire.

7. The implantable cardiac stimulator according to claim 6 wherein said coiled wire is formed in a toroid within said bore.

8. The implantable cardiac stimulator according to claim 6 wherein said coiled wire is braided.

9. The implantable cardiac stimulator according to claim 3 wherein said electrical contact means comprises a plug of electrically conductive polymer.

10. The implantable cardiac stimulator according to claim 2 further comprising an electrically conductive lining within said bore.

11. The implantable cardiac stimulator according to claim 10 wherein said suture point means further comprises electrical contact means inside said lining for securing a reliable electrical contact between said suture point means and an electrically conductive suture.

12. The implantable cardiac stimulator according to claim 2 wherein said stimulator case comprises a header and a hermetically sealed can and wherein said through bore is in said header.

13. The implantable cardiac stimulator according to claim 1 wherein said means for producing a physiologic stimulation to warn said patient comprises means for re-directing an electrical stimulus from the patient's heart to said suture point means.

14. The implantable cardiac stimulator according to claim 13 wherein said suture point means further comprises a through bore in said stimulator case and electrical contact means for securing a reliable electrical contact between said suture point means and an electrically conductive suture.

15. The implantable cardiac stimulator according to claim 14 wherein said electrical contact means comprises at least one spring contact within said bore.

16. The implantable cardiac stimulator according to claim 15 wherein said at least one spring contact comprises a plurality of bristles extending radially inwardly into said bore.

17. The implantable cardiac stimulator according to claim 14 wherein said electrical contact means comprises a coiled wire.

18. The implantable cardiac stimulator according to claim 17 wherein said coiled wire is formed in a toroid within said bore.

19. The implantable cardiac stimulator according to claim 17 wherein said coiled wire is braided.

20. The implantable cardiac stimulator according to claim 14 wherein said electrical contact means comprises a plug of electrically conductive polymer.

21. The implantable cardiac stimulator according to claim 13 wherein said means for re-directing an electrical stimulus comprises a controlled switch.

22. The implantable cardiac stimulator according to claim 21 wherein said means for re-directing an electrical stimulus comprises means for producing a cardiac stimulation therapy at a selected peak voltage level, means for increasing the peak voltage of said therapy producing means beyond a pre-selected voltage, and means responsive to said increased voltage for directing at least part of an electrical current into said suture point means.

23. The implantable cardiac stimulator according to claim 22 wherein said voltage responsive means comprises at least one zener diode.

24. The implantable cardiac stimulator according to claim 14 wherein said stimulator case comprises a header and a hermetically sealed can and wherein said through bore is in said header.

* * * * *